(12) United States Patent
Yano et al.

(10) Patent No.: US 6,866,840 B2
(45) Date of Patent: Mar. 15, 2005

(54) TOOTH-CLEANING COMPOSITION AND METHOD FOR PRODUCING IT

(75) Inventors: Naofumi Yano, Kobe (JP); Hiroyuki Sasaki, Osaka (JP)

(73) Assignee: Kanebo, Ltd., Tokyo (JP)

( * ) Notice: Subject to any disclaimer, the term of this patent is extended or adjusted under 35 U.S.C. 154(b) by 0 days.

(21) Appl. No.: 10/259,231

(22) Filed: Sep. 27, 2002

(65) Prior Publication Data

US 2004/0047813 A1 Mar. 11, 2004

(51) Int. Cl.$^7$ ................................................. A61K 7/16
(52) U.S. Cl. .......................................................... 424/49
(58) Field of Search ........................................... 424/49

(56) References Cited

FOREIGN PATENT DOCUMENTS

| JP | 11-155882 | | 6/1999 |
|---|---|---|---|
| JP | 2001 302428 | * | 10/2001 |
| JP | 2002 293724 | * | 10/2002 |

* cited by examiner

Primary Examiner—Raymond J. Henley, III
Assistant Examiner—Donna Jagoe
(74) Attorney, Agent, or Firm—Hogan & Hartson, LLP

(57) ABSTRACT

The object of the invention is to provide a tooth-cleaning composition capable of well removing staining matters such as tar of tobacco and tea incrustation from teeth merely by cleaning teeth with it in a simplified manner for a short period of time not damaging the surfaces of teeth to thereby estheticize the thus-cleaned teeth, and to provide a method for producing the composition. The object can be attained by a tooth-cleaning composition that contains silicon nitride having a mean particle size of from 0.5 to 10 $\mu$m. The method for producing the tooth-cleaning composition comprises mixing powder of silicon nitride, powder of natural wax, and a solution that contains a water-soluble polymer followed by stirring the resulting mixture until its viscosity at 25° C. reaches from 100,000 to 500,000 cps. Not containing expensive diamond powder but containing silicon nitride powder, a type of ceramics of high hardness, the tooth-cleaning composition of the invention effectively removes staining matters such as tar of tobacco and tea incrustation from teeth merely by cleaning teeth with it in a simplified manner.

1 Claim, No Drawings

US 6,866,840 B2

TOOTH-CLEANING COMPOSITION AND METHOD FOR PRODUCING IT

BACKGROUND OF THE INVENTION

1. Field of the Invention

The present invention relates to a tooth-cleaning composition for cleaning teeth in the mouth, more precisely to such a tooth-cleaning composition capable of easily removing the staining matters such as tar of tobacco and tea incrustation that are between teeth and on their surfaces and thereby estheticizing the thus-cleaned teeth, and to a method for producing the composition.

2. Description of the Related Art

In the field of cleaning teeth, mainly used is a tooth-cleaning composition for brushing teeth with it. However, staining matters such as tar of tobacco and tea incrustation firmly adhere to teeth, and could not be well cleaned from them. A tooth-cleaning composition capable of easily removing the staining matters such as tar of tobacco and tea incrustation that are between teeth and on their surfaces and thereby estheticizing the thus-cleaned teeth is important and necessary for tooth estheticization.

For such a tooth-cleaning composition for removing staining matters such as tar of tobacco and tea incrustation from teeth, heretofore proposed is inorganic powder of, for example, calcium carbonate, calcium phosphate, silica or alumina. However, the inorganic powder is not satisfactory in point of its hardness, and therefore takes much time and labor for satisfactorily attaining its effect of removing tar of tobacco, etc. On the other hand, using diamond powder of the maximum hardness will make it possible to relatively easily remove tar of tobacco and other staining matters from teeth. However, diamond powder is expensive and its use in ordinary tooth-cleaning compositions is problematic as being uneconomical.

On the other hand, we, the present inventors have previously proposed adding silicon nitride to polishing compositions for polishing and glazing the surfaces of various materials in dental treatment (see Japanese Patent Laid-Open No. 155882/1999). Silicon nitride is next to diamond in hardness, and is much more inexpensive than diamond.

SUMMARY OF THE INVENTION

The object of the invention is to provide a tooth-cleaning composition capable of well removing staining matters such as tar of tobacco and tea incrustation from teeth merely by cleaning teeth with it in a simplified manner for a short period of time not damaging the surfaces of teeth to thereby esthethicize the thus-cleaned teeth, and to provide a method for producing the composition.

The object can be attained by a tooth-cleaning composition that contains silicon nitride having a mean particle size of from 0.5 to 10 $\mu$m.

The method for producing the tooth-cleaning composition comprises mixing powder of silicon nitride, powder of natural wax, and a solution that contains a water-soluble polymer followed by stirring the resulting mixture until its viscosity at 25° C. reaches from 100,000 to 500,000 cps.

DETAILED DESCRIPTION OF THE PREFERRED EMBODIMENTS

Silicon nitride for use in the tooth-cleaning composition of the invention has a mean particle size of from 0.5 to 10 $\mu$m. Staining matters having adhered to the surface with fine irregularities of a tooth are difficult to remove from the tooth. For effectively removing such staining matters, used is silicon nitride powder having a mean particle size of not smaller than 0.5 $\mu$m. Coarse silicon nitride particles may damage the surfaces of teeth, and therefore silicon nitride powder having a mean particle size of at most 10 $\mu$m is used.

Silicon nitride is an inorganic compound having a chemical formula $Si_3N_4$. In particular, $\alpha$-type and $\beta$-type crystalline silicon nitride has a Mohs hardness 9, which is next to that of diamond (having a Mohs hardness 10). Accordingly, silicon nitride is usable in dental materials such as composite resin, and in cutting tools, and in machine parts such as bearings, etc. Of inorganic compounds such as alumina and silica, some have a Mohs hardness equivalent to that of silicon nitride. (The same shall apply to the Rockwell hardness and the Vickers hardness of these inorganic compounds.) Like silicon nitride, these may also be used in dental materials, cutting tools, machine parts, etc. However, silicon nitride is superior to these in point of the fracture toughness thereof. For example, the fracture toughness of silicon nitride, measured through SEPB method (according to JIS R1607), is about 6 MPa/m$^{1/2}$, while that of alumina is from 3 to 4 MPa/m$^{1/2}$.

Preferably, the silicon nitride content of the tooth-cleaning composition of the invention falls between 30 and 60% by weight. For better removal of staining matters from teeth with it, the tooth-cleaning composition contains at least 30% by weight of silicon nitride. However, if the silicon nitride content of the tooth-cleaning composition is too high, the viscosity thereof increases. Therefore, the silicon nitride content of the composition is preferably at most 60% by weight in view of the usability of the composition.

Regarding the morphology of the silicon nitride particles to be in the tooth-cleaning composition of the invention, it is desirable that the particles each have a smooth surface and are rounded with no acute-angled edges. More preferably, the particles are spherical.

The tooth-cleaning composition of the invention may contain natural wax. When the composition contains natural wax, the content of the wax component therein may fill up the fine irregularities and cracks in the surface of a tooth and will therefore smooth the tooth surface treated with it. As a result, any additional staining matters are prevented from adhering to the thus-smoothed tooth surface. In addition, the gloss of the tooth surface increases owing to the lustering effect of the wax component.

When the tooth-cleaning composition of the invention contains such natural wax, the content of the wax component in the composition preferably falls between 3 and 10% by weight. It is desirable that the content of the natural wax in the composition is at least 3% by weight for fully ensuring the good gloss of the tooth surface treated with the composition. The natural wax is a hydrophobic substance. If the tooth-cleaning composition contains it too much, the viscosity of the composition increases. Therefore, the content of the natural wax in the tooth-cleaning composition is preferably at most 10% by weight in view of the usability of the composition.

The natural wax component includes carnauba wax extracted from plant, and shellac extracted from coccidae (*Laccifer lacca*). Any of these is generally used as a lustering agent for edibles, cosmetics and medicines. Either singly or as combined, carnauba wax and shellac may be added to the tooth-cleaning composition. Preferably, they are powdery when added to the tooth-cleaning composition. Also preferably, the particle size of the powder is at most 10 μm in order that the powder can be uniformly dispersed in the tooth-cleaning composition.

A hydrophilic solvent of high viscosity may be added to the tooth-cleaning composition of the invention. Containing a high-viscosity hydrophilic solvent, the tooth-cleaning composition becomes slurry or paste, and it prevents silicon nitride powder added thereto from scattering. In addition, since the solvent gives suitable moisture thereto, the slurry or pasty tooth-cleaning composition is easy to use.

When the tooth-cleaning composition of the invention contains such a high-viscosity hydrophilic solvent, the content of the solvent therein preferably falls between 10 and 60% by weight. It is desirable that the content of the high-viscosity hydrophilic solvent in the tooth-cleaning composition is at least 10% by weight in order that the composition may have a suitable viscosity for easy use thereof. In view of the relationship between the amount of the silicon nitride powder in the composition for fully ensuring the effect of the composition to remove staining matters from teeth and the amount of the high-viscosity hydrophilic solvent therein, it is desirable that the amount of the solvent in the composition is at most 60% by weight.

The high-viscosity hydrophilic solvent includes, for example, glycerin, ethylene glycol, polyethylene glycol, propylene glycol, etc. Either singly or as combined, any of these high-viscosity hydrophilic solvents may be added to the tooth-cleaning composition. When the high-viscosity hydrophilic solvent is added to the tooth-cleaning composition, water may be added thereto along with it. Containing water, another advantage of the tooth-cleaning composition is that the mouth having received the composition is easy to wash out.

In case where such a high-viscosity hydrophilic solvent is added to the tooth-cleaning composition of the invention for making the composition slurry or pasty, a water-soluble polymer may also be added thereto. Containing a water-soluble polymer, the viscosity of the tooth-cleaning composition is easy to control and the time-dependent stability thereof is improved.

When a water-soluble polymer is added to the tooth-cleaning composition of the invention, the water-soluble polymer content of the composition preferably falls between 0.5 and 5% by weight. It is desirable that the water-soluble polymer content of the composition is at least 0.5% by weight for preventing the powdery component, e.g., silicon nitride and natural wax in the composition separating from the liquid component, e.g., high-viscosity hydrophilic solvent and water therein, and for preventing the powdery component therein from depositing. Increasing the amount of the water-soluble polymer added to the tooth-cleaning composition results in the increase in the viscosity of the composition. Therefore, in view of the usability of the composition, it is desirable that the water-soluble polymer content of the composition is at most 5% by weight.

The water-soluble polymer includes, for example, those hardly soluble in any others than water, such as hydroxypropylmethyl cellulose, carrageenan, sodium carboxymethyl cellulose, polyvinyl alcohol, methyl cellulose, etc; and those soluble in hydrophilic solvents and in water, such as polyvinylpyrrolidone, etc. Either singly or as combined, these water-soluble polymers may be added to the tooth-cleaning composition. When such a water-soluble polymer is added to the tooth-cleaning composition, it is generally necessary to add a high-viscosity hydrophilic solvent and water thereto. However, when the water-soluble polymer to be added to the composition is soluble in only hydrophilic solvents, adding water to the composition is not indispensable.

In addition to the natural wax, the high-viscosity hydrophilic solvent, the water-soluble polymer and water mentioned above, the tooth-cleaning composition of the invention may further contain, if desired, any other components such as inorganic powder, moisturizer, fragrance, pigment, etc. The inorganic powder includes, for example, calcium carbonate, calcium phosphate, silica, alumina, etc, and it assists the viscosity control of the composition and the removal of staining matters from teeth with the composition. The moisturizer may be a hydrophilic solvent, for example, including aqueous D-sorbitol and glycerin, etc. It gives suitable moisture to the tooth-cleaning composition and plasticizes the composition, and is therefore effective for preventing the composition from being dried and solidified. Fragrance and pigment that may be added to the tooth-cleaning composition may be any ordinary ones generally used in edibles, cosmetics and medicines.

The tooth-cleaning composition of the invention is not specifically defined in point of its morphology, but is preferably powdery, slurry or pasty. In view of its usability, the composition is more preferably slurry or pasty. Even more preferably, the composition has a viscosity of from 100,000 to 500,000 cps (at 25° C.). In case where the composition is powdery, silicon nitride powder may be directly used for it, and, if desired, powder of natural wax and inorganic powder may be added thereto. In case where the composition is slurry or pasty, a high-viscosity hydrophilic solvent may be added to silicon nitride, as so mentioned hereinabove, and also if desired, any other components such as those mentioned hereinabove (any and every acceptable one including, for example, natural wax, water-soluble polymer, water) may be added thereto.

For producing the tooth-cleaning composition of the invention, for example, powder of silicon nitride and powder of natural wax are mixed in a solution that contains a water-soluble polymer, and the resulting mixture is stirred until its viscosity at 25° C. reaches from 100,000 to 500,000 cps. The process realizes the intended, tooth-cleaning composition.

For mixing and stirring the components, usable is any ordinary mixing machine. Briefly, the mixing machine is grouped into three: A type of vessel rotation, in which the vessel itself is rotated, shaken or vibrated; a type of vessel fixation in which the matters are mixed and stirred with a stirring mechanism such as blades fitted therein, or by the action of vapor streams jetted thereinto; and a composite type of combination of the former two. Any of these may be suitably selected for use herein, depending on the morphology of the tooth-cleaning composition to be produced (e.g., powdery, slurry or pasty).

The order of putting the constitutive components into the mixing machine is not specifically defined. For example, powder of silicon nitride and powder of natural wax are previously mixed, and the resulting powder mixture is put into a solution that contains a water-soluble polymer. The process is effective for uniformly mixing and stirring the components. In case where any other powdery components and liquid components are used for producing the tooth-cleaning composition, the group of the powdery components and the group of the liquid components are separately mixed, and then the resulting powder mixture is put into the liquid mixture. The process is also effective for uniformly mixing and stirring the components.

It is desirable that the final viscosity of the tooth-cleaning composition thus produced by mixing and stirring the constituent components falls between 100,000 and 500,000 cps (at 25° C.). The temperature condition in stirring the components is not specifically defined. Preferably, however, the components are stirred at 20 to 30° C. for easily monitoring the viscosity of the resulting composition and for preventing the physical properties of the composition from varying during the process.

EXAMPLES

The invention is described more concretely with reference to the following Examples and Comparative Examples, which, however, are not intended to restrict the scope of the invention.

In the following Examples and Comparative Examples, the method employed for preparing the teeth (to be polished) for evaluating the tooth-cleaning composition tested; the method employed therein for polishing the teeth with the tooth-cleaning composition (polishing operation); and the methods employed therein for evaluating the tooth-cleaning composition tested in point of the Hunter's whiteness increase in the polished teeth, the gloss of the polished teeth, the removal of staining matters from the polished teeth, the scratches in the surfaces of the polished teeth, and the feel of the tooth-cleaning composition in using it for polishing the teeth are all described below.

(1) Preparation of Teeth to be Polished

Having been pulled out, the enamel of each bovine tooth was smoothed with a carborundum paper of #180, and then dipped in a tobacco smoke extract that had been prepared by introducing the smoke of firing 100 tobaccos (trade name, Peace(10) from JAPAN TOBACCO INC.) into 50 ml of distilled water. Thus dipped, the teeth were stored in a thermostat at 37° C. for 1 week. The teeth thus having the staining matters from the tobacco smoke adhered to their surfaces are polished with a sample of tooth-cleaning compositions in the manner mentioned below.

(2) Polishing Operation

A predetermined amount of a sample of tooth-cleaning compositions of Examples and Comparative Examples was applied to the surface of each tooth prepared in the above. Coated with the sample composition, every tooth was polished with a rolling pin of cotton, ASO COTTON SWAB (from ASO PHARMACEUTICAL CO., LTD.). Five operators, three men and two women, carried out the polishing test. Concretely, they polished every sample tooth for 20 strokes/tooth with applying their force thereto in the manner like ordinary teeth brushing operation.

(3) Effect of Removing Staining Matters from Teeth (Hunter's Whiteness Increase, Gloss, Sensual Observation)

Hunter's Whiteness Increase

Before and after the polishing test, the Hunter's whiteness of the enamel surface of each bovine tooth was measured with a spectrometer (model CM-2002: from MINOLTA CO., LTD.). From the data, the Hunter's whiteness increase in every polished tooth was obtained. The Hunter's whiteness increase is an index of the polishing effect of the tooth-cleaning composition tested.

Gloss

The gloss of the enamel surface of each polished bovine tooth was measured with a glossmeter (from MURAKAMI COLOR RESEARCH LABORATORY) at an incident angle of 60°.

Sensual Observation

The five operators that had carried out the polishing test observed the enamel surface of every polished bovine tooth, and sensually evaluated as to whether or not the staining matters were removed from the teeth according to the following criteria:

A: Completely removed.
B: Almost removed.
C: Not removed.

The data of the Hunter's whiteness increase, the gloss and the sensual observation that the five operators had given to every tooth were averaged.

(4) Scratches in the Surfaces of Polished Teeth

Before and after the polishing test, the surface of every tooth was observed through scanning electronic microscopy, and every tooth was sensually evaluated as to whether or not the scratches in the surface of the polished tooth increased according to the criteria mentioned below. The data that the five operators had given to every tooth were averaged.

A: Scratches increased little.
B: Scratches increased.

(5) Feel in Use of Tooth-cleaning Composition

The five operators sensually evaluated every sample of tooth-cleaning compositions as to whether or not the sample was easy to handle and use in their polishing operation, according to the criteria mentioned below. The data that the five operators had given to every tooth were averaged.

A: Having good viscosity, the sample composition was easy to handle and use for polishing the teeth (there was no problem with the sample composition in point of its viscosity).

B: The sample composition was somewhat difficult to apply to the teeth, but there was no problem in polishing the teeth with it.

C: The sample composition was difficult to apply to the teeth and was unfavorable for polishing the teeth (it was too thick and felt dry, or was too thin and readily flowed away).

Examples 1 to 4, Comparative Examples 1 to 3

The samples prepared herein differ in point of the mean particle size of silicon nitride therein.

50% by weight of silicon nitride powder having found to have a smooth surface with no angular edges when observed through scanning electronic microscopy, and having a different mean particle size as in Table 1; 5% by weight of carnauba wax powder, a type of natural wax, having a mean particle size of 5 $\mu$m; a high-viscosity hydrophilic solvent mixture (glycerin/propylene glycol/polyethylene glycol= 18% by weight/4% by weight/6% by weight); a water-soluble polymer mixture (hydroxypropylmethyl cellulose/carrageenan=0.5% by weight/0.5% by weight); 10% by weight of water; and 6% by weight of aqueous sorbitol, a type of moisturizer (70% solution) were well mixed in a stirrer to give slurry or pasty tooth-cleaning compositions. Using these, the bovine teeth prepared in the above were polished, and the test results are give in Table 2.

TABLE 1

|  | Example | | | | Comparative Example | | |
|---|---|---|---|---|---|---|---|
|  | 1 | 2 | 3 | 4 | 1 | 2 | 3 |
| Mean Particle Size ($\mu$m) of Silicon Nitride Powder | 0.5 | 1 | 5 | 10 | 0.1 | 15 | 20 |

TABLE 2

Effect of Removing Staining Matters

| | Hunter's Whiteness Increase | Gloss | Sensual /Observation of Polished Teeth | Scratches in the Surfaces of Polished Teeth | Feel in Use of Sample Composition |
|---|---|---|---|---|---|
| Example 1 | 20 | 47 | A | A | A |
| Example 2 | 22 | 45 | A | A | A |
| Example 3 | 23 | 45 | A | A | A |
| Example 4 | 25 | 41 | A | A | A |
| Comp. Ex. 1 | 16 | 30 | C | A | A |
| Comp. Ex. 2 | 25 | 36 | A | B | A |
| Comp. Ex. 3 | 26 | 34 | A | B | A |

Examples 5 to 8

The samples prepared herein differ in point of the silicon nitride content thereof.

Silicon nitride powder having found to have a smooth surface with no angular edges when observed through scanning electronic microscopy, and having a mean particle size of 1 μm; carnauba wax powder having a mean particle size of 5 μm; a high-viscosity hydrophilic solvent mixture (glycerin/propylene glycol/polyethylene glycol); a water-soluble polymer mixture (hydroxypropylmethyl cellulose/carrageenan); water; and aqueous sorbitol (70% solution) were well mixed in a different ratio as in Table 3, in a stirrer to give slurry or pasty tooth-cleaning compositions. Using these, the bovine teeth prepared in the above were polished, and the test results are give in Table 4.

Examples 9 to 14

The samples prepared herein differ in point of the content of the natural wax therein.

50% by weight of silicon nitride powder having found to have a smooth surface with no angular edges when observed through scanning electronic microscopy, and having a mean particle size of 1 μm; a water-soluble polymer mixture (hydroxypropylmethyl cellulose/carrageenan=0.5% by weight/0.5% by weight); 10% by weight of water; a natural wax mixture component (carnauba wax powder having a mean particle size of 5 μm/shellac powder having a mean particle size of 6 μm); a high-viscosity hydrophilic solvent mixture (glycerin/propylene glycol/polyethylene glycol); and aqueous sorbitol (70% solution) were well mixed in a different ratio as in Table 5, in a stirrer to give slurry or pasty tooth-cleaning compositions. Using these, the bovine teeth prepared in the above were polished, and the test results are give in Table 6.

TABLE 3

(unit: % by weight)

| Example | Silicon Nitride | Carnauba Wax | Glycerin | Propylene Glycol | Polyethylene Glycol | Hydroxypropyl-methyl Cellulose | Carrageenan | Water | Aqueous Sorbitol |
|---|---|---|---|---|---|---|---|---|---|
| 5 | 20 | 5 | 36 | 8 | 12 | 1 | 1 | 11 | 6 |
| 6 | 30 | 5 | 30 | 6 | 10 | 1 | 1 | 11 | 6 |
| 7 | 60 | 5 | 10 | 4 | 5 | 0.5 | 0.5 | 10 | 5 |
| 8 | 70 | 5 | 7 | 2 | 2 | 0.5 | 0.5 | 9 | 4 |

TABLE 4

Effect of Removing Staining Matters

| Example | Hunter's Whiteness Increase | Gloss | Sensual Observation of Polished Teeth | Scratches in the Surfaces of Polished Teeth | Feel in Use of Sample Composition |
|---|---|---|---|---|---|
| 5 | 18 | 38 | B | A | A |
| 6 | 20 | 42 | A | A | A |
| 7 | 22 | 45 | A | A | A |
| 8 | 24 | 44 | A | A | B |

TABLE 5

(unit: % by weight)

| Example | Carnauba Wax | Shellac | Glycerin | Propylene Glycol | Polyethylene Glycol | Aqueous Sorbitol |
|---|---|---|---|---|---|---|
| 9 | 1 | 0 | 20 | 5 | 6 | 7 |
| 10 | 3 | 0 | 19 | 5 | 6 | 6 |
| 11 | 10 | 0 | 14 | 4 | 6 | 5 |
| 12 | 15 | 0 | 10 | 4 | 5 | 5 |
| 13 | 3 | 3 | 17 | 4 | 6 | 6 |
| 14 | 0 | 5 | 18 | 4 | 6 | 6 |

TABLE 6

Effect of Removing Staining Matters

|  | Hunter's Whiteness Increase | Gloss | Sensual Observation of Polished Teeth | Scratches in the Surfaces of Polished Teeth | Feel in Use of Sample Composition |
|---|---|---|---|---|---|
| Example 9 | 21 | 37 | A | A | A |
| Example 10 | 22 | 45 | A | A | A |
| Example 11 | 21 | 48 | A | A | A |
| Example 12 | 22 | 49 | A | A | B |
| Example 13 | 21 | 45 | A | A | A |
| Example 14 | 21 | 43 | A | A | A |

Examples 15 to 21

The samples prepared herein differ in point of the high-viscosity hydrophilic solvent content thereof.

Silicon nitride powder having found to have a smooth surface with no angular edges when observed through scanning electronic microscopy, and having a mean particle size of 1 μm; carnauba wax powder having a mean particle size of 5 μm; a high-viscosity hydrophilic solvent mixture (glycerin/propylene glycol/polyethylene glycol/ethylene glycol); a water-soluble polymer mixture (hydroxypropylmethyl cellulose/carrageenan); water; and aqueous sorbitol (70% solution) were well mixed in a different ratio as in Table 7, in a stirrer to give slurry or pasty tooth-cleaning compositions. Using these, the bovine teeth prepared in the above were polished, and the test results are give in Table 8.

TABLE 7

(unit: % by weight)

| Example | Silicon Nitride | Carnauba Wax | Glycerin | Propylene Glycol | Polyethylene Glycol | Ethylene Glycol | Hydroxypropyl-methyl Cellulose | Carrageenan | Water | Aqueous Sorbitol |
|---|---|---|---|---|---|---|---|---|---|---|
| 15 | 50 | 5 | 5 | 0 | 0 | 0 | 1 | 1 | 31 | 7 |
| 16 | 50 | 5 | 10 | 0 | 0 | 0 | 1 | 1 | 26 | 7 |
| 17 | 50 | 5 | 30 | 0 | 0 | 0 | 0.5 | 0.5 | 8 | 6 |
| 18 | 30 | 3 | 60 | 0 | 0 | 0 | 0.5 | 0.5 | 6 | 0 |
| 19 | 20 | 3 | 70 | 0 | 0 | 0 | 0.5 | 0.5 | 6 | 0 |
| 20 | 50 | 5 | 0 | 10 | 10 | 10 | 0.5 | 0.5 | 8 | 6 |
| 21 | 50 | 5 | 5 | 5 | 5 | 5 | 0.5 | 0.5 | 17 | 7 |

TABLE 8

Effect of Removing Staining Matters

|  | Hunter's Whiteness Increase | Gloss | Sensual Observation of Polished Teeth | Scratches in the Surfaces of Polished Teeth | Feel in Use of Sample Composition |
|---|---|---|---|---|---|
| Example 15 | 22 | 45 | A | A | B |
| Example 16 | 21 | 44 | A | A | A |
| Example 17 | 22 | 44 | A | A | A |
| Example 18 | 20 | 42 | A | A | A |

TABLE 8-continued

| | Effect of Removing Staining Matters | | | | |
|---|---|---|---|---|---|
| | Hunter's Whiteness Increase | Gloss | Sensual Observation of Polished Teeth | Scratches in the Surfaces of Polished Teeth | Feel in Use of Sample Composition |
| Example 19 | 17 | 37 | B | A | B |
| Example 20 | 21 | 44 | A | A | A |
| Example 21 | 21 | 42 | A | A | A |

Examples 22 to 28

The samples prepared herein differ in point of the water-soluble polymer content thereof:

50% by weight of silicon nitride powder having found to have a smooth surface with no angular edges when observed through scanning electronic microscopy, and having a mean particle size of 1 μm; 5% by weight of carnauba wax powder having a mean particle size of 5 μm; a high-viscosity hydrophilic solvent mixture (glycerin/propylene glycol/polyethylene glycol); a water-soluble polymer mixture (hydroxypropylmethyl cellulose/polyvinylpyrrolidone); water; aqueous sorbitol (70% solution); and inorganic powder (silica powder having a mean particle size of 4 μm) were well mixed in a different ratio as in Table 9, in a stirrer to give slurry or pasty tooth-cleaning compositions. Using these, the bovine teeth prepared in the above were polished, and the test results are give in Table 10.

TABLE 9

(unit: % by weight)

| Example | Glycerin | Propylene Glycol | Polyethylene Glycol | Hydroxypropylmethyl Cellulose | Polyvinyl-pyrrolidone | Water | Aqueous Sorbitol | Silica |
|---|---|---|---|---|---|---|---|---|
| 22 | 18 | 4 | 6 | 0.1 | 0 | 10.9 | 6 | 0 |
| 23 | 18 | 4 | 6 | 0.5 | 0 | 10.5 | 6 | 0 |
| 24 | 16 | 4 | 6 | 3 | 0 | 10 | 6 | 0 |
| 25 | 15 | 4 | 5 | 5 | 0 | 10 | 6 | 0 |
| 26 | 13 | 3 | 4 | 10 | 0 | 10 | 5 | 0 |
| 27 | 24 | 5 | 9 | 0 | 1 | 0 | 6 | 0 |
| 28 | 20 | 5 | 7 | 0 | 2 | 0 | 6 | 5 |

TABLE 10

| | Effect of Removing Staining Matters | | | | |
|---|---|---|---|---|---|
| | Hunter's Whiteness Increase | Gloss | Sensual Observation of Polished Teeth | Scratches in the Surfaces of Polished Teeth | Feel in Use of Sample Composition |
| Example 22 | 20 | 42 | A | A | B |
| Example 23 | 21 | 43 | A | A | A |
| Example 24 | 21 | 42 | A | A | A |
| Example 25 | 21 | 41 | A | A | A |
| Example 26 | 20 | 40 | A | A | B |
| Example 27 | 22 | 44 | A | A | A |
| Example 28 | 23 | 45 | A | A | A |

Examples 29 to 33

These are to demonstrate other samples of the tooth-cleaning composition of the invention.

Silicon nitride powder having found to have a smooth surface with no angular edges when observed through scanning electronic microscopy, and having a mean particle size of 1 μm; carnauba wax powder having a mean particle size of 5 μm; and a high-viscosity hydrophilic solvent (glycerin) were well mixed in a different ratio as in Table 11, in a stirrer to give slurry or pasty tooth-cleaning compositions. Using these, the bovine teeth prepared in the above were polished, and the test results are give in Table 12.

TABLE 11

(unit: % by weight)

| Example | Silicon Nitride | Carnauba Wax | Glycerin | Water |
|---|---|---|---|---|
| 29 | 50 | 0 | 37.5 | 12.5 |
| 30 | 74 | 0 | 19.5 | 6.5 |
| 31 | 69 | 3 | 21 | 7 |
| 32 | 68 | 6 | 19.5 | 6.5 |
| 33 | 57 | 16 | 20.25 | 6.75 |

TABLE 12

| | Effect of Removing Staining Matters | | | | |
|---|---|---|---|---|---|
| | Hunter's Whiteness Increase | Gloss | Sensual Observation of Polished Teeth | Scratches in the Surfaces of Polished Teeth | Feel in Use of Sample Composition |
| Example 29 | 21 | 44 | A | A | B |
| Example 30 | 28 | 36 | A | A | B |
| Example 31 | 26 | 40 | A | A | B |
| Example 32 | 23 | 45 | A | A | B |
| Example 33 | 20 | 49 | A | A | B |

Comparative Examples 4 to 6

The samples prepared herein do not contain silicon nitride.

Slurry tooth-cleaning compositions were prepared in the same manner as in Example 30, except that synthetic spherical silica powder having a mean particle size of 1.5 μm was used in Comparative Example 4 and that synthetic spherical alumina powder having a mean particle size of 0.7 μm was used in Comparative Example 5, in place of the silicon nitride in Example 30. The sample of Comparative Example 6 is a commercially-available tooth-cleaning composition that is exclusively for tar of tobacco removal from teeth. Using these, the bovine teeth prepared in the above were polished, and the test results are give in Table 13.

TABLE 13

| | Effect of Removing Staining Matters | | | | |
|---|---|---|---|---|---|
| | Hunter's Whiteness Increase | Gloss | Sensual Observation of Polished Teeth | Scratches in the Surfaces of Polished Teeth | Feel in Use of Sample Composition |
| Comp. Ex. 4 | 13 | 23 | C | A | A |
| Comp. Ex. 5 | 15 | 26 | C | A | A |
| Comp. Ex. 6 | 12 | 9 | C | A | A |

What is claimed is:

1. A method for producing a tooth-cleaning composition for removing staining matters from teeth, which comprises mixing powder of silicon nitride, powder of natural wax, and a solution that contains a water-soluble polymer followed by stirring the resulting mixture until its viscosity at 25° C. reaches from 100,000 to 500,000 cps.

* * * * *